United States Patent [19]
Herbert et al.

[11] Patent Number: 5,868,771
[45] Date of Patent: Feb. 9, 1999

[54] SCALPEL BLADE COVER

[75] Inventors: H. Nicholas Herbert, San Juan Capistrano, Calif.; Russell R. Lyons, Days Creek, Oreg.; Arkadiusz A. Strokosz, Laguna Niguel, Calif.

[73] Assignee: Pabban Development, Inc., Irvine, Calif.

[21] Appl. No.: 900,570

[22] Filed: Jul. 25, 1997

[51] Int. Cl.$^6$ .................................................. A61B 17/32
[52] U.S. Cl. .............................. 606/167; 30/162; 30/286
[58] Field of Search .................................. 606/167, 172; 30/162, 286, 163

[56] References Cited

U.S. PATENT DOCUMENTS

| | | | |
|---|---|---|---|
| 3,171,201 | 3/1965 | Carifi | 30/335 |
| 3,906,626 | 9/1975 | Riuli | 30/162 |
| 5,496,340 | 3/1996 | Abidin et al. | 606/167 |

OTHER PUBLICATIONS

Mueller "The Surgical Armamentarium" Surgical Instrument Catalog p. 3, 1980.

*Primary Examiner*—Michael H. Thaler
*Attorney, Agent, or Firm*—G. Donald Weber, Jr.

[57] ABSTRACT

A scalpel blade sheath which encloses and retains a scalpel blade therein. A scalpel handle is selectively inserted into the sheath whereby the scalpel blade is securely attached to the scalpel handle in preparation for cutting operations. The sheath is selectively slipped onto the scalpel handle to expose the blade for the cutting operation. The sheath is repositioned over the scalpel blade to protect the blade (and the user thereof) when the cutting operation is concluded. When the blade is to be removed from the scalpel handle after the cutting operation, the scalpel blade is retained within the sheath for safe and sanitary disposal of the blade and the sheath.

18 Claims, 3 Drawing Sheets

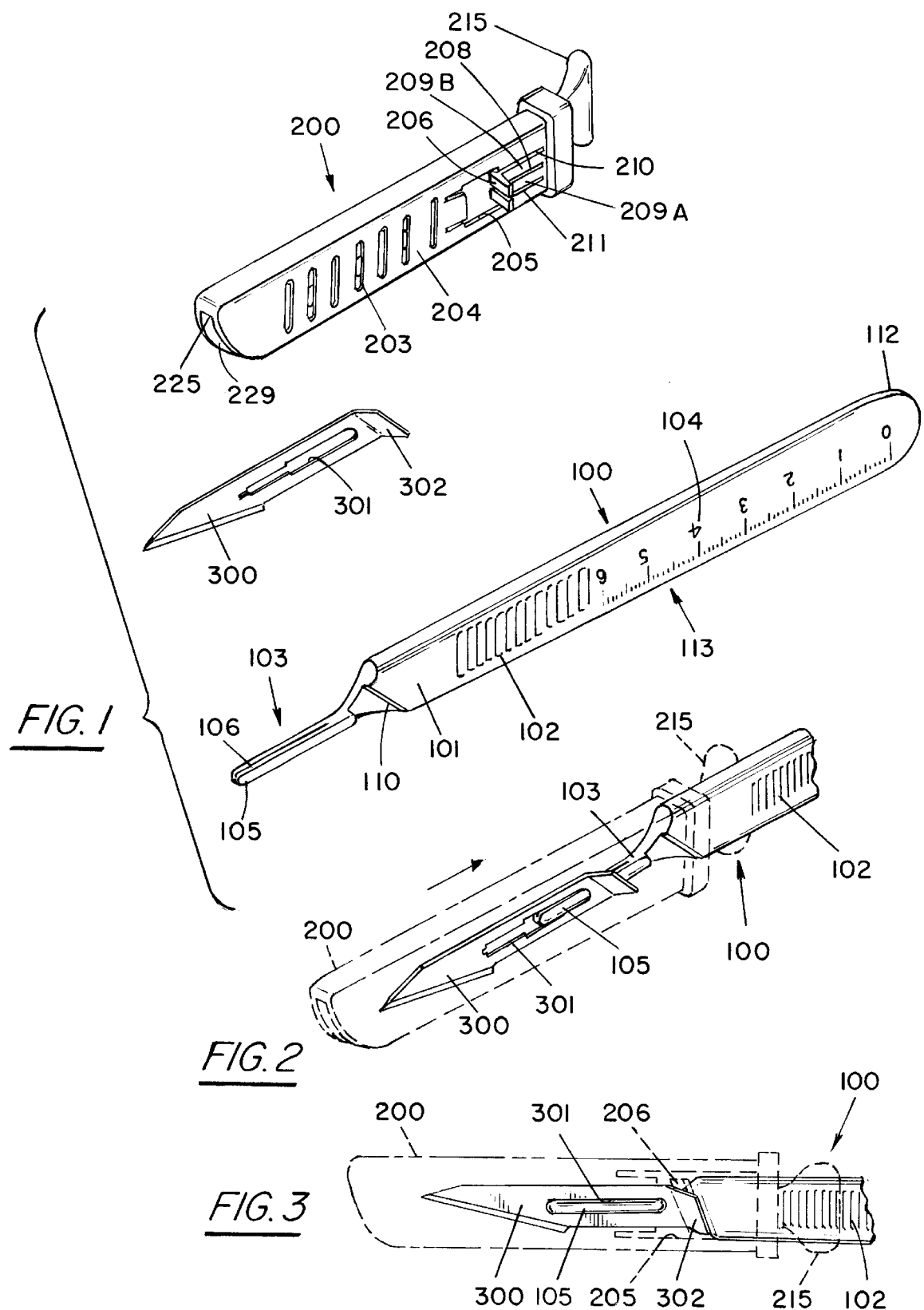

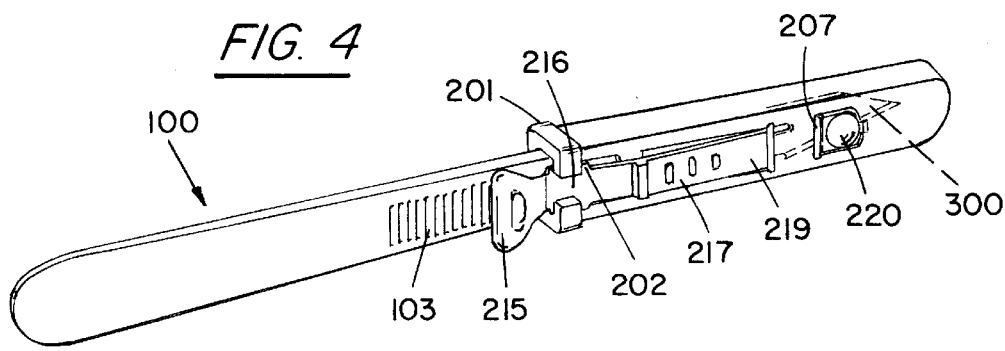
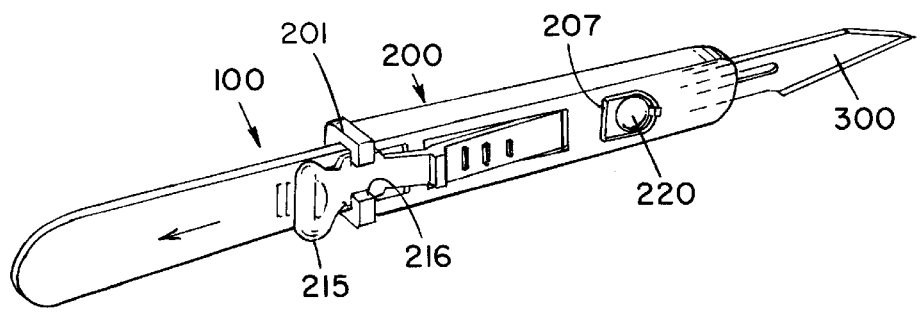
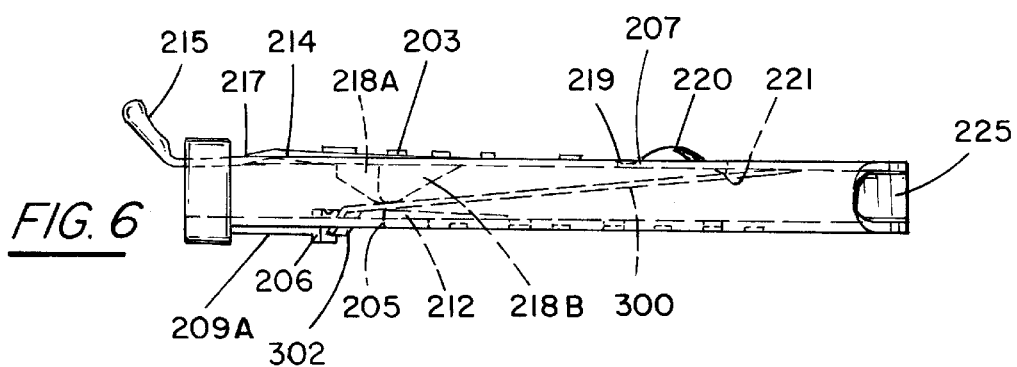
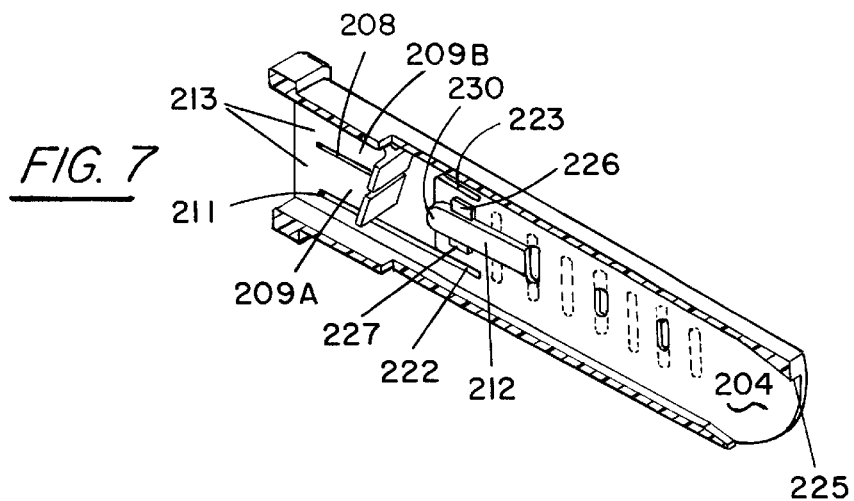

SCALPEL BLADE COVER

BACKGROUND

1. Field of the Invention

The invention concerns medical-surgical instruments such as scalpels, in general, and a sheath for safely and securely enclosing a scalpel blade, in particular.

2. Prior Art

Although surgical scalpels have been in use for centuries, there has been little in the way of advancement of the basic design thereof. In recent years, the commercially-important surgical scalpels have been those having disposable blade portions. In this type of scalpel, the blade component is detachable from the handle component and disposed of by deposit in a special container, for example, which may thereafter be handled without hazard. It will be appreciated, however, that such disposable surgical scalpel blades still present a hazard to the individual who must detach and transfer the blade component.

Demand by hospital administrators and liability insurance carriers for a disposable scalpel and/or scalpel blade has increased considerably in recent years because of the potential for transmission of serious diseases. The ultimate in desirability is a surgical scalpel blade which may be disposed of safely and securely.

Attempts to satisfy the need have been made. For example, some surgical knives comprise a hollow handle component having a slidably extensible blade therein. In effect, the latter instruments employ the handle component as a sheath for the blade component when not in use. Typically, such sheathable blade assemblies are not contemplated for disposal after a single use. Furthermore, such cutting instruments do not provide a positive means for preventing the unsheathing of the blade portion by a careless handler when disposal of the blade is desired.

PRIOR ART STATEMENT

Listed herewith are patents which relate to scalpels and scalpel guards known in the art. The patents are listed in numerical order with no significance attached thereto.

U.S. Pat. No. 3,906,626; DISPOSABLE SURGICAL SCALPEL; A. Riuili. This patent discloses a unitary disposable surgical scalpel which has a sheath for permanently sheathing the blade.

U.S. Pat. No. 4,735,202; MICROSURGICAL KNIFE WITH LOCKING BLADE GUARD; R. W. Williams. This patent is directed to a disposable microsurgical knife having a blade guard that can be locked into a blade covering position and easily removed therefrom.

U.S. Pat. No. 5,071,426); SURGICAL SCALPEL WITH RETRACTABLE BLADE GUARD; S. Dolgin et al. This patent is directed to a scalpel with a blade guard which is mounted for movement between a blade guarded position and a blade exposed position.

U.S. Pat. No. 5,139,507; SURGICAL SCALPEL WITH RETRACTABLE BLADE GUARD; S. Dolgin et al. This patent is directed to a scalpel with a blade guard which is mounted for movement between a blade guarded position and a blade exposed position.

U.S. Pat. No. 5,250,063; SURGICAL SCALPEL WITH RETRACTABLE GUARD; M. R. Abidin et al. This patent is directed to a surgical scalpel which is provided with a retractable guard for the cutting blade thereof.

U.S. Pat. No. 5,275,606; GUARDED SCALPEL FOR SURGICAL USE; M. R. Abidin et al. This patent is directed to a surgical scalpel which is provided with a retractable guard for the cutting blade thereof.

U.S. Pat. No. 5,292,329; RETRACTABLE SURGICAL KNIFE; R. S. Werner. This patent is directed to a retractable scalpel provided with a latch mechanism wherein the scalpel is automatically retracted when not in use by pushing a latch mechanism.

U.S. Pat. No. 5,309,641; DISPOSABLE SURGICAL SCALPEL WITH SAFETY GUARD; J. W. Wonderley et al. This patent discloses a scalpel including an elongated handle having a blade carried adjacent one end of the handle and a guard mounted to the handle for a sliding movement.

U.S. Pat. No. 5,330,492; SAFETY SCALPEL; D. L. Haugen. This patent is directed to a surgical instrument including a blade fixed to the forward end of a handle and a spring bias retractable sheath which is received within the handle.

U.S. Pat. No. 5,342,379; SAFETY SCALPEL; F. G. Volinsky. This patent is directed to a safety scalpel which includes a disposable cartridge and a permanent handle.

U.S. Pat. No. 5,370,654; DISPBSABLE GUARDED FINGER SCALPEL FOR INSERTING A LINE IN A PATIENT AND METHOD OF USE THEREOF; M. R. Abidin. This patent is directed to a disposable finger scalpel which includes a frame which provides a guard for a blade.

SUMMARY OF THE INSTANT INVENTION

The surgical scalpel of this invention includes a sheath for the blade component which reduces the risks and hazards of blade handling. Once sheathed, access to the blade component is prevented thereby assuring that the scalpel blade will not present a hazard to individuals charged with ultimate disposal of the scalpel blade.

This invention relates to a scalpel blade sheath which encloses and securely retains a scalpel blade therein. The sheath is selectively placed in engagement with an end of a scalpel handle whereby the scalpel blade within the sheath is securely attached to the scalpel handle while the blade is encased within the sheath. The sheath is caused to slide onto the scalpel handle thereby exposing the scalpel blade for utilization. The sheath is then replaced in engagement with the scalpel blade by sliding the sheath off the scalpel handle. The scalpel blade is selectively removed from engagement with the scalpel handle while the blade is still within the sheath. The scalpel blade is then retained in the sheath for further use or for safe and sanitary disposal of the blade within the sheath.

BRIEF DESCRIPTION OF THE DRAWINGS

FIG. 1 is an exploded view of one embodiment of the blade and sheath of the instant invention together with a typical scalpel handle.

FIG. 2 is a perspective view of the blade and sheath of the instant invention interacting with a scalpel handle.

FIG. 3 is a plan view of the blade and sheath of the instant invention attached to a scalpel handle.

FIG. 4 is a perspective view of the blade and sheath of the instant invention together with a scalpel handle and arranged in the guarded condition.

FIG. 5 is a perspective view of the blade and sheath of FIG. 4 with the sheath withdrawn and the blade exposed.

FIG. 6 is a partially broken away view of the blade and sheath combination of the instant invention.

FIG. 7 is a perspective, broken away view of one side of the interior of the sheath with the opposite surface of the sheath removed.

DESCRIPTION OF A PREFERRED EMBODIMENT

Figure 8:
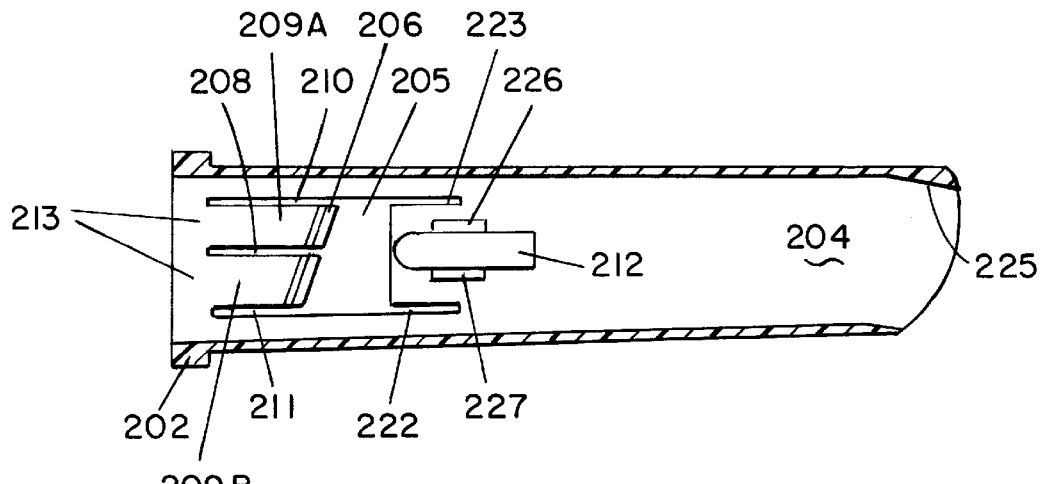
FIG. 8 is a plan view of the interior of the sheath shown in FIG. 7.

Referring now to FIG. 1, there is shown an exploded view of one embodiment of the blade and sheath of the instant invention together with a typical scalpel handle.

In particular, the scalpel handle 100 is of conventional shape and configuration. This handle is, typically, made of stainless steel or other suitable material. Typically, the distal end 112 is relatively thin while the gripping or middle portion 113 is somewhat thicker. The front end 103 of the scalpel handle generally takes the configuration of an extended nose 105 which is relatively narrow and includes the groove 106 on at least one edge thereof for receiving a blade as described hereinafter.

Typically, the scalpel handle 100 can taper in width towards the distal end. On at least one of the surfaces 101, the scalpel handle typically includes a plurality of ridges 102 or slots transverse to the longer axis thereof. In some embodiments, other indicia 104 such as centimeter indicators or the like can be engraved on the handle.

Typically, the distal end 112 of the handle 100 is somewhat rounded for convenience. In addition, a shoulder 110 can be provided at the end of the scalpel adjacent to the inner end of the nose 105.

The sheath 200 is also disclosed. While not necessarily limited thereto, the sheath 200 is typically formed of a transparent plastic material such as a conventional polymer material including polystyrene, polycarbonate, polyurethane, polyethelene, phenol-formaldehyde resins, polybutylene and the like.

In one embodiment, the sheath is approximately 2¼ inches long by about ½ inch wide. The sheath wall is about 20 mils thick with an opening (or channel) extending axially therethrough.

As shown in FIG. 1, a plurality of substantially parallel, transverse strips 203 are provided across the outer surface of the sheath. These strips (or ridges) can be raised or depressed areas in the body of the sheath. The strips 203 provide additional traction or gripping surface for the user of the sheath.

An aperture 205 having an irregular (but nearly pentagonal) shape is provided through the upper surface 204 of the sheath. The aperture 205 is shaped to include a diagonal base edge 206 in order to correspond to and cooperate with the conventional diagonal end of a scalpel blade described infra.

Openings 208, 210 and 211 are formed in the upper surface of the sheath 100. These openings or slits provide the required flex of ribs 209A and 209B as the sheath rides back onto the handle.

A stop 225 is provided at the front end of sheath 200 to limit the movement of the sheath relative to the scalpel handle.

The ends of ribs 209A and 209B form the diagonal base edge 206 of opening 205 to prevent the end of the scalpel blade from passing through sheath 200 when it is pushed forward to remove the sheath and blade from the handle.

Thumb button 215 is provided on the opposite surface of sheath 200 as described infra. The thumb button is used to push or pull the sheath 200 relative to the handle 100.

A representative blade 300 is shown. The shape of the cutting edge of the blade and so forth are representative only. It is well known that there are many sizes, shapes and styles of scalpel blades. The invention described herein is intended to cooperate with virtually any blade shape.

Typically, the blade 300 includes a slot 301 which is configured to cooperate with and engage the nose 105 of the handle. Typically, the nose is inserted into the larger portion of the slot 301 and slid forward to engage the smaller end of the slot in the groove 106 in the nose.

In the blade shown in FIG. 1, the distal end 302 defines a diagonal end. In addition, the end 302 is bent at approximately a 20° angle relative to the body of the blade. This bent end is configured to interact with the diagonal base edge 206 formed by ribs 209A and 209B of the sheath 200.

Because the sizes, shapes and bend angles of the blades may vary, separate ribs 209A and 209B are shown for flexibility. Thus, edge 206 is split for easy fit between the bent edge of the blade. Of course, it is contemplated that ribs 209A and 209B can be combined as a single unitary rib. In this case, the middle slot 210 could be eliminated.

In FIG. 2, scalpel blade 300 is shown along with the position thereof relative to the sheath 200, shown in dashed or phantom lines. The blade 300 is stored within the sheath 200 for safe and secure handling thereof without a danger of harm to the handler of the blade.

When the blade 300 (within sheath 200) is to be attached to handle 100, the front end 103 of the handle (which is conventionally shaped) is inserted into the right end (in this showing) of the sheath 200 adjacent to the mounting end of the blade 300. The elongated nose 105 of the handle is inserted into and mates with the slot 301 in the blade in conventional fashion. The sheath 200 and blade 300 are then pulled over the scalpel handle 100 in the direction of the arrow (to the right in this case) in order to secure the blade 300 to the nose end 105 of the scalpel handle in conventional fashion while maintaining the blade 300 within the sheath 200.

Referring now to FIG. 3, there is shown the condition wherein the blade 300 is fully mounted onto the nose 105 of the handle 100. The sheath 200 (shown in dashed outline) covers the blade 300 and a portion of the scalpel handle 100. The bent end 302 of the blade is shown interacting with the diagonal edge 206 of aperture 205 in the sheath. The edge 206 is formed by the ends of the ribs 209A and 209B (see FIG. 1).

Referring now to FIG. 4, there is shown a perspective view of the sheath 200 and blade 300 mounted on the handle 100. This view is taken from the opposite side of the unit shown in FIGS. 2 and/or 3. In FIG. 4, the blade 300 is shown, in dashed outline, within the sheath 200. It is seen that the blade 300 is attached to the handle 100 but is completely covered by the sheath 200 to prevent any inadvertent or accidental cutting by the blade. In this view, the thumb button 215 is shown at the distal end of the sheath. The thumb button 215 is attached to the thumb button extension 217 which is mounted to the sheath 200 by a living hinge 219. The thumb button 215 (and thumb button extension 217) moves freely but is retained within the sheath 200 by the shoulders 202 on the sheath edge 201 which define the slot 216 at the end of the sheath.

In addition, a button tab 220 is provided in the surface of sheath 200 adjacent to the blade 300. This button tab 220 is, also, mounted in the nature of a living hinge 207 which flexes slightly relative to the sheath. The button tab 220 provides a restraint for the sheath 200 relative to the handle 100 as described infra.

Referring now to FIG. 5, there is shown a perspective view of the unit shown in FIG. 4 with the sheath 200 retracted to expose the blade 300 for any suitable cutting purposes. It is understood that the blade 300 is securely fastened to the scalpel handle 100 as described above. The sheath has been withdrawn along the handle by exerting pressue on the thumb button 215. Typically, the thumb button 215 is operated by pulling thereon by the user's thumb. The thumb button extension 217 is flexed slightly outwardly by downward pressure of thumb button 215 and then by the insertion of a handle into the sheath.

In the preferred embodiment, the button tab 220 includes a tip 221 at the frontal portion thereof which extends inwardly relative to the sheath (see FIG. 6) and selectively engages the ribs (or strips) 103 in the scalpel handle. This arrangement provides additional security to prevent the sheath 200 from inadvertently sliding back over and covering the blade during a cutting procedure.

When the cutting procedure is concluded, the sheath 200 is repositioned over the blade 300 by pressing on the thumb button 215 and forcing the sheath back over the blade into the position shown in FIG. 4. In this operation, the thumb button extension 217 is free to fold outwardly from the sheath and away from the blade 300 as will become clear infra. In this case, the force inserted on the sheath is sufficient to override the restraint caused by the button tab 220 and the protruding point.

When the sheath is returned to the position shown in FIG. 4, the blade 300 is covered and the scalpel device can be handled in any appropriate fashion without fear of an accidental cut therefrom.

When it is desired to remove the blade 300 from the handle 100, the sheath 200 is moved back (to the right) over the blade and adjacent to the end of the blade as mounted on the handle (as shown in FIG. 4). The thumb button extension 217, which has been pushed outwardly relative to the sheath by the handle, is pressed inwardly by the user to engage the body of the scalpel blade. By pressing on the extension 217, the mounting end 302 of the blade is moved away from the handle 100 (by cams 218 shown in FIGS. 6, 9 and 10). The sheath and blade are then moved forward so that the blade slides out of the groove 106 formed in the nose 105 at the handle end. Thus, the mounting end of the blade 300 is, effectively, disengaged from the scalpel handle. The distal end 302 of blade 300 extends into aperture 205 in the surface 204 of the sheath 200 and is then engaged with the edge 206 of the ribs 209A and 209B. Thus, the blade travels with the sheath and is retained therein as the sheath is moved off and away from the scalpel handle. At this juncture, the blade is completely disengaged from the handle. Also, the blade is retained completely within the sheath 200. Consequently, no sharp edges of the blade are exposed or accessible to the user wherein the blade can be disposed of safely.

Referring now to FIG. 6, there is shown a partially broken away plan view of the sheath 200. The ribs 203 are shown on the upper and lower surfaces of sheath 200 to provide the gripping or traction attribute. Again, the ribs may be raised or depressed. (Note that references to upper and lower surfaces are merely relative and are not absolutes.) In this case, the strips 203 (or ribs) are shown aligned with each other, but this is not necessarily the case. Rather, this is a matter of the ease and the economy of manufacturing. Also, the ribs can be replaced by raised dots or buttons and may be located on only one surface of the sheath. If desired, the ribs 203 can be omitted altogether.

The opening 205 is shown in the lower surface of the sheath 200. The end of 209A and 209B protrude over opening 205 to form edge 206 which will encounter the distal end 302 of blade 300 to prevent the blade from passing through the end of the sheath 200 when the sheath and blade are being removed from handle 100. The ribs 209A and 209B, as noted, can take the form of one or more fingers (see FIG. 1) in order to properly engage the end of the blade.

A small ramp 212 (see also FIGS. 7 and 8) extends into the internal space of the sheath from the inner surface of the bottom of the sheath. The ramp 212 engages the wide part of slot 301 to drag blade 300 back onto nose 105 as the sheath is pulled back onto the handle. Two smaller ramps, i.e. ramps 226 and 227 (see FIG. 7) on either side of ramp 212 keep the blade at the proper angle for fitting onto handle 100 while cams 218 push on the other side of the blade.

The thumb button extension 217 is also shown to have a hinged connection 219 with the upper surface of sheath 200. In addition, the extension 217 includes a hinged portion 214 at a midpoint thereof. This hinge 214 (also a living hinge for thumb button 215) allows the extension 217 to ride up onto the handle 100 when a scalpel handle is inserted into the sheath as described hereinafter. The extension 217 includes the internal cams 218 which, in this case, are shown as generally triangular in configuration.

Again, the button tab 220 is shown with the point 221 depending therefrom. As noted, this tab is flexibly mounted to the sheath by a living hinge and selectively interacts with and engages the scalpel handle. For example, the point 221 engages the ridges 102 on the handle 100 to inhibit relative movement of the handle and the sheath.

Referring now to FIGS. 7 and 8, there are shown interior views of the lower portion of sheath 200 (as shown in FIG. 6.) In these views, the inner surface of the sheath 200 is shown relatively smooth for convenience in manufacture and in utilization.

The living hinge 213 for ribs 209A and 209B is shown attached to or integral with the surface 204 of the blade sheath. The ramp 212 is shown formed as part of the inner surface of the sheath. The ramp 212 is slightly displaceable because the slots 222 on either side thereof renders the ramp slightly flexible. The rounded end 230 of ramp 212 selectively engages slot 301 in blade 300. The ramps 226 and 227, typically, include an angled surface in order to maintain the blade 300 in a preferred position within the sheath. The pentagonal opening 205 in the surface 204 of the sheath is shown as are the side slots 210 and 211 related to ribs 209A and 209B.

The slots 210 and 211 provide for flex of ribs 209A and 209B of the upper surface as sheath is pushed back onto the handle. Likewise, the slots 222 and 223 on either side of ramp 212 permit flexure of the ramp 212, as well.

The stop 225 is shown at the front end of the sheath. This stop is utilized to prevent the handle from passing through the sheath in the event that the handle is slightly smaller than typical.

Figure 9:
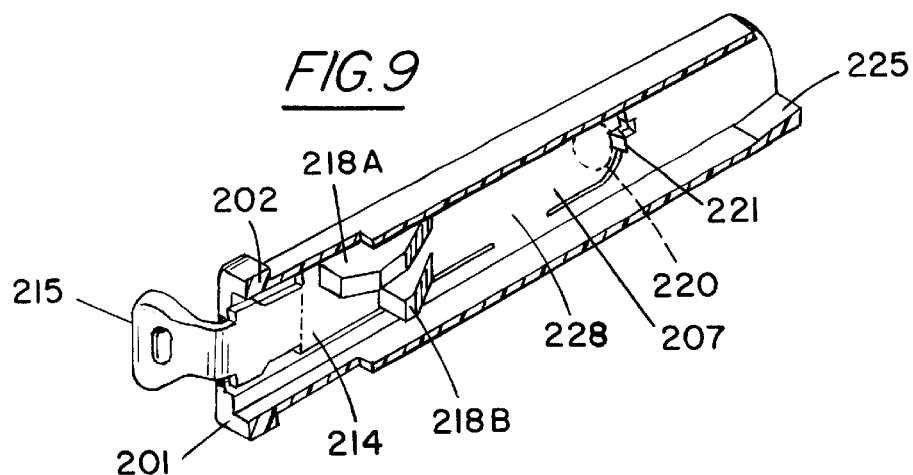
FIG. 9 is a perspective, broken away view of the other side of the interior of the sheath with the opposite surface of the sheath removed.
Figure 10:
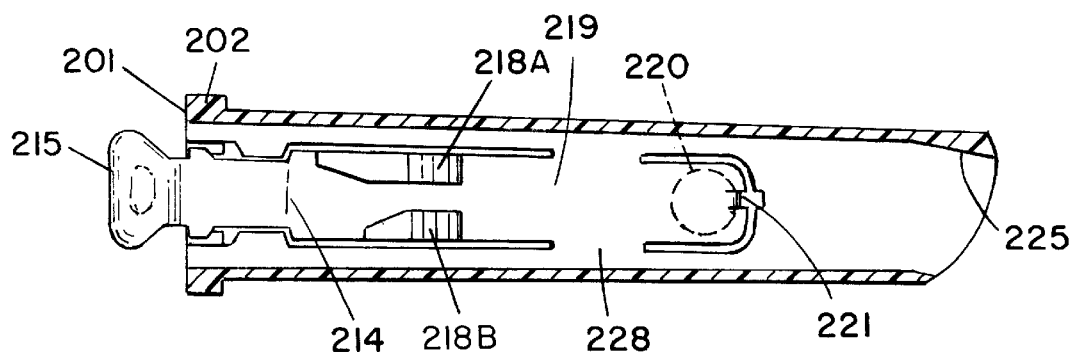
FIG. 10 is a plan view of the interior of the sheath shown in FIG. 9.

Referring now to FIGS. 9 and 10, there is shown an interior view of the upper portion of sheath 100 (as shown in FIG. 6). In this view, the thumb button 215 and extension 217 are shown mounted, essentially, flush with the outer surface 204 of the sheath 200. In this view, the thumb button 215 is shown at the distal end of the sheath. The thumb button 215 is attached to the thumb button extension 217 which is mounted to the sheath by a living hinge technique. The thumb button (and thumb button extension) moves freely but is retained within the sheath 200 by the shoulders 202 on the sheath edge 201 which define the slot 216 at the distal end of the sheath. In addition, the extension 217 includes a hinged portion 214 at a midpoint thereof. This hinge 214 allows the extension to ride up onto the handle when a scalpel handle is inserted into the sheath as described hereinafter. Thus, the extension 217 can hingedly move both inwardly and outwardly relative to the sheath. The inner surface of the extension 217 includes the pair of cams 218A and 218B which extend inwardly relative to the sheath.

The cams 218A and 218B are designed to extend along the inner surface of extension 217 and straddle the nose end 105 of the scalpel handle. The cams 218A and 218B bear upon the mounting end 302 of the blade when the extension 217 is pressed inwardly. The cams 218A and 218B on the tab are properly dimensioned so as to push the mounting end of the blade away from the mounting nose end 105 of the handle when pressed.

Again, the button tab 220 is shown with the point 221 depending therefrom. As noted, this tab is flexibly mounted in sheath 200 by means of a living hinge 207 and selectively interacts with and engages the scalpel handle.

The stop 225 is shown at the front end of the sheath to prevent the handle from passing through the sheath as noted supra.

Thus, there is shown and described a unique design and concept of a scalpel blade cover. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

We claim:

1. A sheath for retaining a blade comprising, an elongated housing comprising an upper surface, a lower surface and two side surfaces connecting the upper and lower surfaces together, an aperture through said upper surface, a hinged tab movably mounted in said lower surface aligned opposite said aperture through said upper surface, said tab including at least one cam on the inner surface thereof which can selectively interact with said aperture when said hinged tab is moved.

2. The sheath recited in claim 1 including, flexible rib means formed in said upper surface adjacent to said aperture.

3. The sheath recited in claim 2 wherein, said flexible rib means includes a diagonal end thereof which defines one side of said aperture.

4. The sheath recited in claim 2 wherein, said flexible rib means comprises a plurality of individual flexible fingers.

5. The sheath recited in claim 1 including, blade ramp means formed on the interior of said upper surface adjacent to said aperture to position a blade within said housing.

6. The sheath recited in claim 1 wherein, said tab includes an elongated flexible tab extension.

7. The sheath recited in claim 6 wherein, said elongated flexible tab extension includes a hinge at approximately the mid point thereof.

8. The sheath recited in claim 1 including, a blade movably mounted between said upper and lower surfaces in said housing.

9. The sheath recited in claim 8 wherein, said blade includes a cutting edge, a bent end, and a mounting slot therethrough, said mounting slot adapted to received and engage a blade handle.

10. The sheath recited in claim 1 including, button tab means hingedly mounted to said lower surface adjacent to said tab.

11. The sheath recited in claim 10 wherein, said button tab means includes a latch member at one end thereof.

12. The sheath recited in claim 11 wherein, said latch member is adapted to engage a blade handle which has been inserted into said sheath.

13. The sheath recited in claim 10 wherein, said button tab means is mounted to said lower surface by a living hinge.

14. The sheath recited in claim 1 wherein, said sheath is fabricated of a plastic material.

15. The sheath recited in claim 1 including, stop means at one end of at least one of said upper surface and said lower surface to limit the passage of a blade handle through the interior space of said sheath.

16. The sheath recited in claim 1 wherein, said hinged tab is mounted in said lower surface by a living hinge.

17. The sheath recited in claim 1 including, at least one rib on at least one of said upper and lower surfaces of said housing.

18. The sheath recited in claim 1 wherein, said cam comprises at least one generally triangular cam.

* * * * *